United States Patent [19]

Sato

[11] Patent Number: 4,655,764
[45] Date of Patent: Apr. 7, 1987

[54] MEDICAL NEEDLE ASSEMBLY AND MEDICAL DEVICE INCORPORATING THE SAME

[75] Inventor: Isao Sato, Yamanashi, Japan

[73] Assignee: Terumo Corporation, Tokyo, Japan

[21] Appl. No.: 899,786

[22] Filed: Aug. 22, 1986

Related U.S. Application Data

[63] Continuation of Ser. No. 587,237, Mar. 7, 1984, abandoned.

[30] Foreign Application Priority Data

Mar. 11, 1983 [JP] Japan .................................. 58-40299

[51] Int. Cl.$^4$ ............................................. A61B 19/00
[52] U.S. Cl. ..................................... 604/408; 604/111; 604/905
[58] Field of Search ................................ 604/408–414, 604/192, 263, 110, 111, 243, 905

[56] References Cited

U.S. PATENT DOCUMENTS 3,994,412 10/1976 Difiglio ............................... 604/410
4,435,177 3/1984 Kuhlemann ........................ 604/408

Primary Examiner—John D. Yasko
Attorney, Agent, or Firm—Frishauf, Holtz, Goodman & Woodward

[57] ABSTRACT

The present invention provides a medical needle assembly comprising in part a hub and a protector, each discrete from the other and having a lumen passing continuously therethrough. A hollow needle is enclosed within the continuous lumens and fixed to the base of the protector. A thin-walled weak point for separation of the hub and protector is provided near to the periphery of the area of hub and protector attachment. The hub and protector are attached using a solvent capable of dissolving the hub and protector materials, or an adhesive, the use of a plasticized vinyl chloride polymer paste resin being especially desirable. The present invention also provides a medical device in which the above medical needle assembly is incorporated in, and forms part of, a tubing line connected to a container holding blood.

2 Claims, 8 Drawing Figures

MEDICAL NEEDLE ASSEMBLY AND MEDICAL DEVICE INCORPORATING THE SAME

This application is a continuation of application Ser. No. 587,237, filed 3/7/84 now abandoned.

BACKGROUND OF THE INVENTION

1. Field of the Invention

The present invention relates to a medical needle assembly, and a medical device incorporating the same in the tubing line between a needle inserted into the blood donor's vein and a blood bag, and so comprised as to permit the collection of a blood sample for testing following the collection of blood in the blood bag.

2. Description of the Prior Art

Samples of blood collected from a donor in a blood bag are collected with evacuated sampling tubes and other devices for a variety of determinations. As with blood collection in a blood bag, this must be done under contamination-free conditions. Many medical needle assemblies, and medical devices incorporating the same in the tubing line connecting the blood bag and the venipuncture needle, have been developed for this reason. Typical of these are U.S. Pat. Nos. 3,127,892, 3,217,710, and 3,342,179. In U.S. Pat. No. 3,127,892, the junction consists of two rubber sleeves that couple with each other by means of a protruding ring and a matching groove that interengage; the two sleeves separate when pulled apart by hand. This type of arrangement has a number of disadvantages. First, because the rubber sleeves are joined by the interengagement of a ring and a groove, the tensile strength is less than about 500 grams, resulting in a weak coupling force. This means that during production or use, the sleeves may separate, presenting a risk of fluid leakage or bacterial contamination. Moreover, as the two sleeves are merely interengaged, it is difficult to check whether the sleeves have been disengaged and separated prior to use. Hence, this type of arrangement is not adequately tamper-proof.

In U.S. Pat. Nos. 3,217,710 and 3,342,179, the hub assembly incorporating the needle consists of two integrally formed sections provided therebetween with a "weak" or "breaking" point. At the required time, the two sections are twisted apart and used. This arrangement makes it easy to check whether the device has been opened prior to use, and is therefore tamper-proof. However, because the breaking strength of the thin-walled weak point formed between the two sections is not uniform, and is at times too large, wings have been added to aid in twisting the two sections apart.

Although integral formation of the hub and protector appears to be a reasonable approach, this in fact presents a host of problems. To begin with, the formation of a long, thin-walled composite hub and protector requires a high level of technical sophistication. Accordingly, it is difficult to form a small, thin-walled weak point. The inevitable result is a tendency to make the point that should be thin-walled relatively thick instead. This means that a greater force is required to twist-snap the two sections apart, which tends to decrease product uniformity. In addition, precise production molds must be used, raising costs.

OBJECT OF THE INVENTION

An object of the present invention is to provide an inexpensive inner needle assembly, and a medical device incorporating the same, that is relatively easy to manufacture and has a uniform, thin-walled weak point for snapping apart so that the assembly can easily be broken open with the application of a given force, and the hollow needle exposed.

SUMMARY OF THE INVENTION

According to a first aspect of the invention, there is provided an inner needle assembly comprising a hollow needle with a pointed tip, a hub that supports the base of the hollow needle and is at the base connectable to a section of tubing such as to communicate with the hollow needle, and a protector consisting of a hollow body with a lumen that extends continuously from the base to the tip thereof, said hollow body being attached at the base to the tip of said hub such as to sealingly enclose that portion of the hollow needle that projects from said hub, and being connectable at the tip to another section of tubing such as to communicate with said continuous lumen, and wherein a thin-walled weak point for the separation of said hub and said protector is provided near to but outside the periphery of the area of hub and protector attachment.

According to a second aspect of the invention, there is provided a medical device comprising a container for holding fluid; a medical needle assembly that includes a hollow needle with a pointed tip, a hub that supports the base of said hollow needle and is at the base connectable to a first section of tubing such as to communicate with said hollow needle, and a protector consisting of a hollow body with a lumen that extends continuously from the base to the tip thereof, said hollow body being attached at the base to the tip of said hub such as to sealingly enclose that portion of the hollow needle that projects from said hub, and being connectable at the tip to a second section of tubing such as to communicate with said continuous lumen, and wherein a thin-walled weak point for the separation of said hub and said protector is provided near to but outside the periphery of the area of hub and protector attachment; a puncture needle; a first section of tubing one end of which is connected to the base of said hub such as to communicate with said hollow needle, and the other end of which is connected to said puncture needle in fluid communication; and a second section of tubing one end of which is connected to the tip of said protector such as to communicate with the continuous lumen of said protector, and the other end of which is connected to said fluid container in fluid communication.

In the invention as described above, the hub and protector should preferably be made of the same materials, and the hub and protector should be attached using a solvent capable of dissolving the materials of which these two members are made, or an adhesive. Especially desirable as said adhesive is a plasticized vinyl chloride polymer paste resin.

BRIEF DESCRIPTION OF THE DRAWINGS

For fuller understanding of the objects and advantages of the present invention, reference should be made to the following detailed description of the preferred embodiments represented in the accompanying drawings wherein.

DESCRIPTION OF THE PREFERRED EMBODIMENTS

Figure 2:
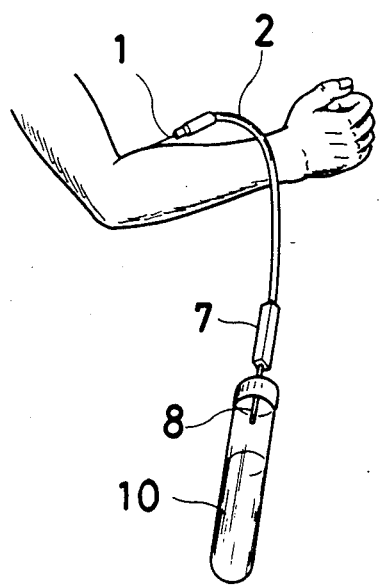
FIGS. 1 and 2 are drawings respectively showing a first and a second mode of use of a medical needle assembly according to the present invention.
Figure 1:
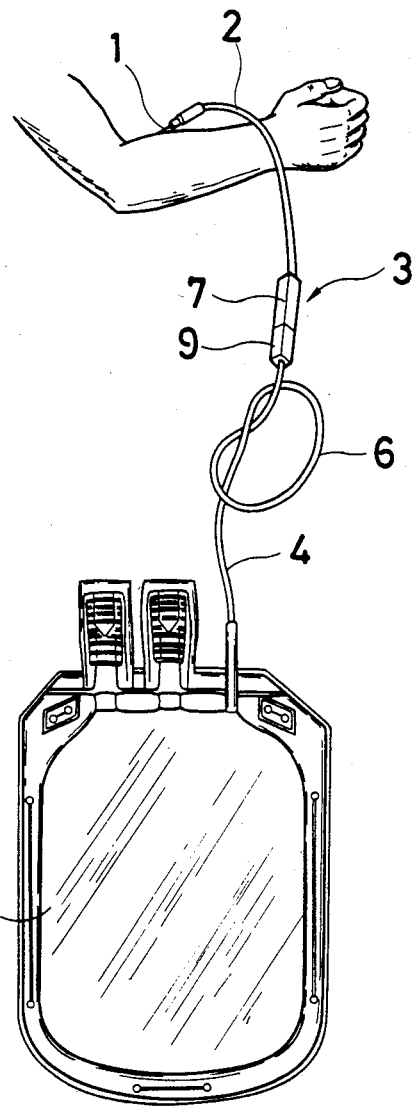

As shown in FIG. 1, during blood collection, puncture needle 1 is inserted in the donor's vein, and blood is collected in blood bag 5 after passing through a first section of tubing 2, a medical needle assembly 3, and a second section of tubing 4. Once a sufficient quantity of blood has been collected in the blood bag, the knot 6 in the second section of tubing 4 is tightened, stopping blood flow. Medical needle assembly 3 is then opened, and the needle 8 embedded in the hub 7 removed from a protector 9. Next, as shown in FIG. 2, needle 8 is inserted into an evacuated or other, similar type of blood sampling tube 10, and a blood sample collected. Medical needle assembly 3 thus must: (1) assure a blood flow path to the blood bag that is free from contamination during blood collection, and (2) be easy to open and use when taking a blood sample.

However, in the past, as already noted, the mechanism for dissociating the hub and protector of the medical needle assembly has presented a number of problems, both during manufacture and use, and has not been entirely satisfactory. To resolve this, the medical needle assembly of the present invention is constructed as follows.

Figure 3:
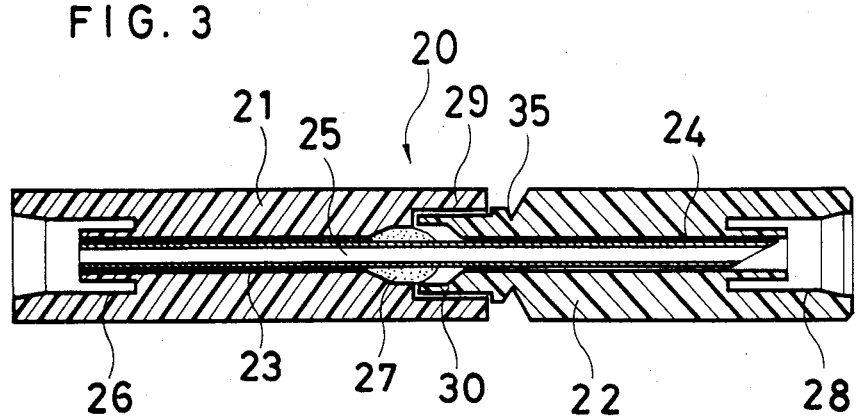
FIGS. 3, 4, 5, and 6 are fragmentary sectional views of various embodiments of the medical needle assembly according to the present invention.

As is shown in FIG. 3, the medical needle assembly 20 of the present invention consists of a hub 21 and a protector 22, within the respective continuous lumens 23 and 24 of which is enclosed a hollow needle 25, and the hub and protector attached together. An annular recess 26 is formed at the base of hub 21 in order to permit the tubing to communicatively connect to the hub. The base of hollow needle 25 is bonded with adhesive 27 within lumen 23 of the hub, and the pointed tip of hollow needle 25 projects out from hub 21. The projecting portion of hollow needle 25 is held free of movement or play within lumen 24 of protector 22. An annular recess 28 like that at the base of hub 21 is formed at the tip of protector 22 to allow the tubing to communicatively connect to the tip of the protector.

Figure 4:
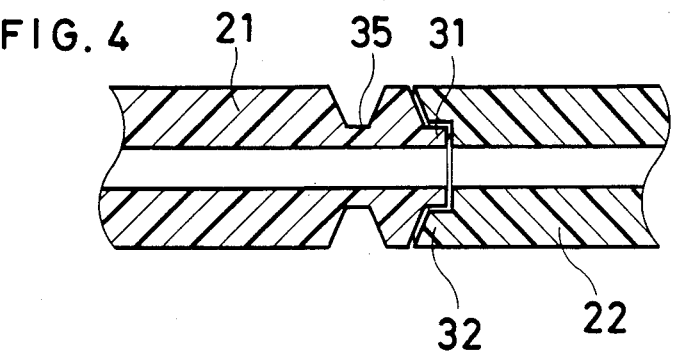
Figure 5:
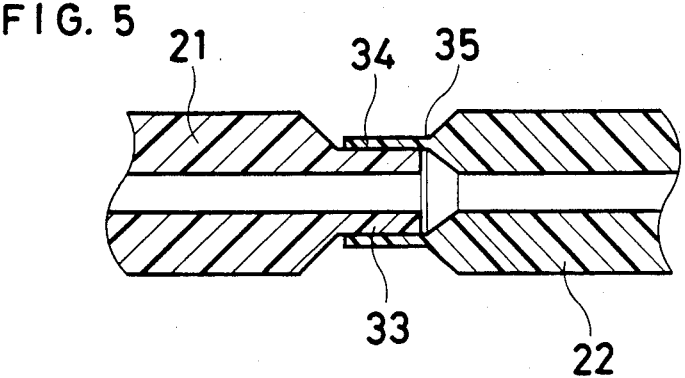

The attachment of hub 21 with protector 22 should preferably be done using a solvent capable of dissolving the materials making up the hub and protector, or an adhesive. In the embodiment shown in FIG. 3, attachment is done between the annular projection 29 on the hub and the annular projection 30 of smaller diameter on the protector. In the embodiment depicted in FIG. 4, attachment occurs between the projection 31 of small diameter on the hub and the projection 32 of large diameter on the protector, while in the embodiment of FIG. 5, attachment takes place between the projection 33 of small diameter on the hub and the thin-walled projection 34 on the protector. Because the tubing used for connection is generally made of polvinyl chloride (PVC), this material is used in the hub as well. Hence, the protector bonded to the hub should also be made of PVC. Organic solvents such as, typically, tetrahydrofuran (THF) may be used as the solvent for attaching the hub with the protector. The following type of vinyl chloride polymer paste resin may be used as the adhesive.

The vinyl chloride polymer paste resin used in the present invention is obtained by the uniform dispersion and suspension of a fine vinyl chloride polymer powder having a particle size of 0.02-20 $\mu$m, and preferably 0.1-10 $\mu$m, in plasticizer. In addition to vinyl chloride homopolymer, copolymers consisting of vinyl chloride and comonomers such as vinylidene chloride, vinyl acetate, and vinyl alcohol may also be used as the powdered vinyl chloride copolymer. When said copolymer is used, the amount of comonomer bonded with the vinyl chloride should be no more than 30 mol %, and preferably 3-7 mol %. The average molecular weight of this homopolymer or copolymer should be 900-1200, and preferably 960-1130.

Because the paste resin is formed by the dispersion and suspension of this type of powdered vinyl chloride copolymer in plasticizer, the paste resin should contain 25-50% by weight, and preferably 30-50% by weight, of solids. Examples of the plasticizer that may be used for the suspension of this vinyl chloride polymer include phthalates such as di-2-ethylhexyl phthalate, di-n-octyl phthalate, diisooctyl phthalate, diheptyl phthalate, didecyl phthalate, diisodecyl phthalate, octyldecyl phthalate, and butylbenzyl phthalate, trimellitates such as tributyl trimellitate and trioctyl trimellitate, aliphatic polybasic acid esters such as dioctyl adipate, dioctyl azelate, and dioctyl sebacate, phosphate esters such as tricresyl phosphate, trixylenyl phosphate, monooctyldiphenyl phosphate, monobutyldixylenyl phosphate, and trioctyl phosphate, citrates such as tributylacetyl citrate, trioctylacetyl citrate, and tributyl citrate, and butylphthalylbutyl glycolate.

The adhesive used in the present invention is prepared into a sol by further compounding from 50 to 350 parts by weight, but preferably 150-200 parts, and most preferably about 200 parts, of plasticizer per 100 parts by weight of the above type of paste resin. Compounds of the type cited above may be used as the plasticizer. If the amount of plasticizer per 100 parts by weight of paste resin is less than 50 parts, the adhesive sol used has inadequate viscosity. If, on the other hand, the amount of plasticizer exceeds 350 parts by weight, this results in an inadequate bonding strength.

Where necessary, stabilizers such as metallic soaps consisting of metals such as lead, cadmium, barium, zinc, and calcium in combination with stearic acid, lauric acid, ricinolic acid, naphthenic acid, and 2-ethylhexoic acid or the like, or organotin compounds such as dibutyltin dilaurate, dibutyltin dimaleate, and dibutyltin mercaptide and the like may be added to the above formulation of vinyl chloride paste resin and plasticizer.

The use of a paste resin has the following advantages. (1) When solvent-type adhesives are used, there is always the possibility of residual solvent being extracted or migrating into pharmaceutical solution or blood, and eventually entering the human body; paste resins eliminate this problem. (2) When the hub and protector are both made of PVC, because the adhesive is also made of the same resin, the adhesive layer has an indefinite boundary, providing improved fluid tightness. Another reason for improved fluid tightness over solvent-type adhesives is that the paste resin powder absorbs the plasticizer in which it is dispersed, helping to fill the gap between the hub and protector. (3) Since solvents evaporate quickly, solvent-type adhesives may finish curing before the hub is fully engaged with the protector. The resulting attachment is often liable to fluid leakage. (4) If epoxy adhesives are subjected to autoclave sterilization prior to complete curing, they swell, which adversely affects the bond between the hub and protector. (5) When a paste resin adhesive is used, the required bond strength may be obtained during assembly fabrication even if the adhesive incompletely cures at room temperature. This is because the adhesive is completely heat-cured during autoclave sterilization after the hub has been fully engaged with the protector.

In the above-described medical needle assembly of the present invention in which the hub and protector are attached by bonding, the snap-apart or twist-apart mechanism consists of a thin-walled weak point of the type described below. Any of a variety of specific constructions may be selected for use as the snap-apart mechanism. Typical examples are described below in connection with FIGS. 3 to 6.

In the embodiment shown in FIG. 3, a ring-like notch has been cut into the annular projection 30 on the protector 22 at a point distal to the area of attachment of hub 21 and protector 22 to form a thin-walled weak point 35. In the embodiment shown in FIG. 4, a ring-like notch has been cut in hub 21 at a point proximal to the area of attachment of hub 21 and protector 22 to form a thin-walled weak point 35. In this case, the adhesive used to attach the hollow needle to the hub must be placed closer towards the first section of tubing than the thin-walled weak point 35 on the hub. In the embodiment shown in FIG. 5, the distal portion of a thin annular extension 34 from protector 22 not used for the attachment of hub 21 and protector 22 serves as thin-walled weak point 35. In the embodiment shown in FIG. 6, the protector 22 has a thin annular wall 35 which is engageable in an annular groove 40 at the tip of the hub 21. A weak point in the form of a V-shaped notch 35 is formed in the outer wall of the protector 22 at a position near to but outside the area of attachment between the protector annular wall 35 and the hub groove 40.

In the preferred embodiments of the present invention, the weak point is in the form of a notch which is V shaped in axial cross section. Preferably, the notch 35 is of a V shape having an angle of inclusion of at least 40°, and more preferably between 50° and 90°. A V-shaped notch is preferable because chips or water droplets may collect within the notch during machining or steam sterilization in an autoclave. Air is generally blown over the entire medical device to remove such foreign matter before the device is packaged. A V-shaped notch with an angle of less than 40° tends to prevent air blown over the device from entering the notch and clearing away foreign matter. On the other hand, a V-shaped notch with an included angle of more than 90° may sometimes be disadvantageous because that portion of the hub or protector which is near to but apart from the point of hub-protector separation during twisting becomes relatively thin-walled, reducing the strength of the entire needle assembly. In addition, during twisting, the torque is not concentrated at the base of the V-shaped notch and may result in deformation of the hub or protector.

These thin-walled weak points can be uniformly and precisely formed during molding of the individual parts or by subsequent machining, permitting dissociation of the hub and protector when required by twisting or pulling apart with a fixed and uniform force. In this way, compared with conventional products in which both the hub and protector are formed integrally, by attaching together a hub and protector having a preformed thin-walled weak point, a thinner weak point can be uniformly fabricated without requiring the production mold to be as precise. In turn, this vastly increases the reliability with which the inner needle assembly can be dissociated. Furthermore, greater allowance is permitted in the dimensions of the junction between the hub and protector because the gap between the two is filled with adhesive when these are joined during assembly.

Figure 7:
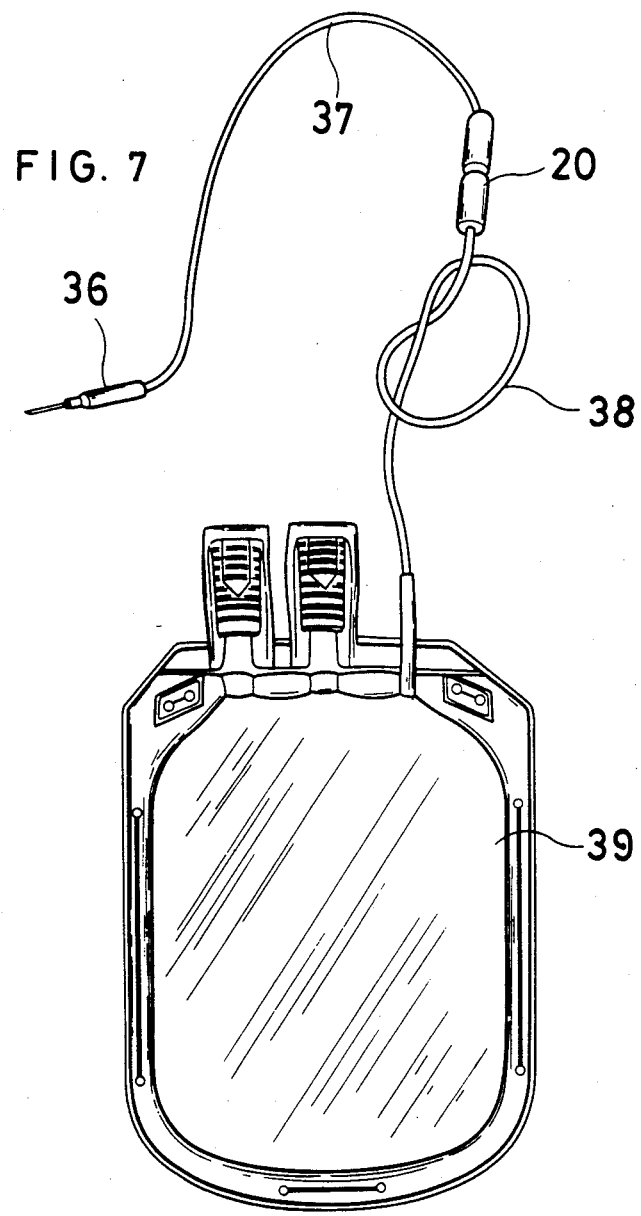
FIG. 7 is a schematic planar view of a medical device incorporating a medical needle assembly according to the present invention.

This medical needle assembly 20 may be connected to and used with a variety of blood containers. FIG. 7 shows schematically a typical case in which the needle assembly is connected to a blood bag. FIG. 7 shows a blood-collecting needle, 36, a first section of tubing 37, a second section of tubing 38, and a blood bag 39. The component parts of the medical device of the present invention may be joined and attached in the same manner as described earlier for the attachment of the hub 21 and protector 22 of medical needle assembly 20. The use of a vinyl chloride polymer paste resin is especially desirable.

In addition to vinyl chloride homopolymer, copolymers consisting of vinyl chloride with vinylidene chloride, vinyl acetate, vinyl alcohol, or the like may also be used as the vinyl chloride resin of which the blood bag or other blood sampling container, and connection tubing are made. When using these copolymers, the amount of monomer bonded with the vinyl chloride should be no more than 15 mol %, and preferably 3–7 mol %.

OPERATION OF THE INVENTION

A brief description of the operation and use of the medical device of the present invention is given below to aid in a fuller understanding of its features.

Concerning the medical device depicted in FIG. 7, as shown in FIG. 1, during blood collection, puncture needle 1 is inserted in the donor's vein, and blood is collected in blood bag 5 after passing through the first section of tubing 2, medical needle assembly 3, and the second section of tubing 4. Once a sufficient quantity of blood has been collected in the blood bag, the knot 6 on the second piece of tubing 4 is tightened, stopping blood flow. Medical needle assembly 3 is then opened, and needle 8 embedded in hub 7 removed from the protector 9. Next, as shown in FIG. 2, needle 8 is inserted in an evacuated or other, similar type of blood sampling tube 10, and a blood sample collected.

Figure 8:
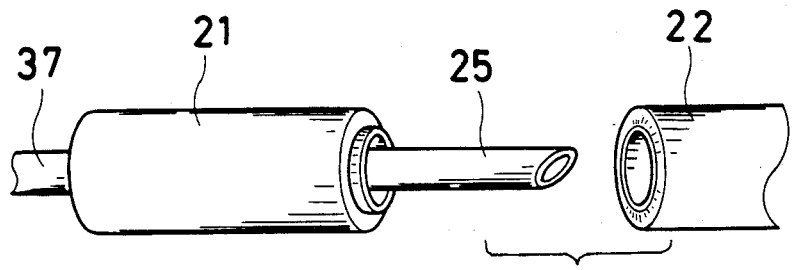
FIG. 8 is an oblique view showing one example of a medical needle assembly according to the present invention after being opened.
Figure 6:
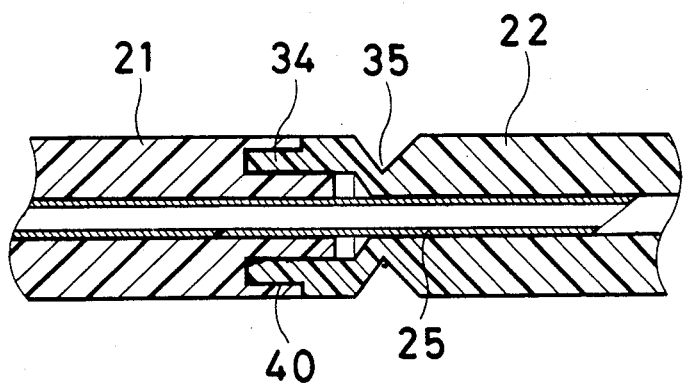

The medical needle assembly is opened by means of the mechanism shown in FIGS. 3 to 6. This is done by placing the fingers on ribs [not shown] formed on both hub 21 and protector 22, then twisting apart in opposite directions. A portion not forming a part of the area of attachment of the hub 21 and protector 22, i.e., a ring-like thin-walled weak point 35 formed just adjacent to the area of attachment between hub 21 and protector 22, is twisted and snapped, and the hub and protector separated. The removal of protector 22 causes the hollow needle 25 to be exposed. FIG. 8 shows one example of the needle assembly after it has been opened, and the hub and protector separated.

EFFECTS OF THE INVENTION

The medical needle assembly and medical device incorporating said needle assembly according to the present invention have a large number of advantages over conventional products, several of which are as follows.

(1) The hub and protector are not formed integrally, but are joined together as separate parts. When a vinyl chloride polymer paste resin, for example, is employed to bond the hub and protector together, the use of solvent becomes unnecessary. As a result, there is no deterioration of the material or crack formation, and there are no adverse effects on the work environment in the bonding process.

(2) Not as much precision is required in the production molds as when the hub and protector are formed integrally, in addition to which the production of the thin-walled weak point ceases to be a problem. Moreover, compared to when the hub and protector are formed integrally, the thin-walled weak point can be made thin enough that dissociation by twisting and snapping at the time of use is uniform for all products, without associated damage during shipping and distribution.

(3) When attachment of the protector and hub involves the joining of identical materials, a good, strong bond can be formed.

What we claim is:

1. A medical needle assembly:
a hollow needle having a pointed tip and a base;
a hub having a base and a tip end for supporting the base of said hollow needle so that the tip of said hollow needle projects from the tip end of said hub, the base of said hub being connectable to a section of tubing to communicate the tubing with the interior of said hollow needle; and
a protector including a hollow body having a base and a tip end, and a lumen that extends continuously from the base to the tip end of said hollow body, said hollow body being attached at its base to the tip end of said hub to sealingly enclose that portion of the hollow needle that projects from said hub, and being connected at its tip end to one end of said second section of tubing to communicate said second section of tubing with said continuous lumen of said protector,
said hub and said protector both being made of polyvinyl chloride, and
an adhesive at the area of attachment of said base of said hollow body to said tip end of said hub to secure said hollow body to said hub, said adhesive being a plasticized vinyl chloride polymer paste resin, said adhesive being applied as a sol comprising 100 parts by weight of a polyvinyl chloride paste resin in which a vinyl chloride polymer powder is dispersed and suspended in a plasticizer to a solids content of 25 to 50% by weight, and 50 to 350 parts by weight of a plasticizer,
wherein a thin-walled weak point for the separation of said hub and said protector is provided near to but outside the periphery of the area of hub and protector attachment, and wherein the thin-walled weak point is a notch that is V-shaped in axial cross section and said V-shaped notch has an angle of inclusion of from about 50° to about 90°.

2. A medical device, comprising:
a container for holding fluid;
first and second sections of tubing, each of which has opposite ends;
a medical needle assembly including:
a hollow needle having a pointed tip and a base,
a hub having a base and a tip end for supporting the base of said hollow needle so that the tip of said hollow needle projects from the tip end of said hub, the base of said hub being connected to one end of said first section of tubing to communicate said first section of tubing with the interior of said hollow needle,
a protector including a hollow body having a base and a tip end, and a lumen that extends continuously from the base to the tip end of said hollow body, said hollow body being attached at its base to the tip end of said hub to sealingly enclose that portion of the hollow needle that projects from said hub, and being connected at its tip end to one end of said second section of tubing to communicate said second section of tubing with said continuous lumen of said protector, said hub and said protector both being made of polyvinyl chloride, and
an adhesive at the area of attachment of said base of said hollow body to said tip end of said hub to secure said hollow body to said hub, said adhesive being a plasticized vinyl chloride polymer paste resin,
said adhesive being applied as a sol comprising 100 parts by weight of a polyvinyl chloride paste resin in which a vinyl chloride polymer powder is dispersed and suspended in a plasticizer to a solids content of 25 to 50% by wieght, and 50 to 350 parts by weight of a plasticizer, and
wherein a thin-walled weak point for the separation of said hub and said protector is provided near to but outside the periphery of the area of hub and protector attachment, and wherein the thin-walled weak point is a notch that is V-shaped in axial cross section and said V-shaped notch has an angle of inclusion of from about 50° to about 90°;
a puncture needle;
said first section of tubing having another end which is connected to said puncture needle in fluid communication therewith; and
said second section of tubing having another end which is connected to said fluid container in fluid communication therewith.

* * * * *

UNITED STATES PATENT AND TRADEMARK OFFICE
CERTIFICATE OF CORRECTION

PATENT NO. : 4,655,764

DATED : April 7, 1987

INVENTOR(S) : I. SATO

It is certified that error appears in the above-identified patent and that said Letters Patent is hereby corrected as shown below:

Column 8, line 39, "wieght" should read -- weight --

Column 5, lines 32 and 37, "35" should read -- 34 --

Signed and Sealed this

Sixteenth Day of February, 1988

Attest:

DONALD J. QUIGG

*Attesting Officer*　　　　　*Commissioner of Patents and Trademarks*